United States Patent [19]

Ma et al.

[11] Patent Number: 5,610,517
[45] Date of Patent: Mar. 11, 1997

[54] METHOD AND APPARATUS FOR DETECTING FLAWS BELOW THE SURFACE OF AN ELECTRICALLY CONDUCTIVE OBJECT

[75] Inventors: Yu P. Ma, Nashville; John P. Wikswo, Jr., Brentwood, both of Tenn.

[73] Assignee: Vanderbilt University, Nashville, Tenn.

[21] Appl. No.: 472,558

[22] Filed: Jun. 7, 1995

[51] Int. Cl.$^6$ .................................................. G01N 27/90
[52] U.S. Cl. .......................... 324/233; 324/220; 324/225; 324/232; 324/240
[58] Field of Search ...................................... 324/220, 221, 324/225, 228, 232, 233, 240–242, 248

[56] References Cited

U.S. PATENT DOCUMENTS

| | | | |
|---|---|---|---|
| 2,881,387 | 4/1959 | Wood | 324/241 |
| 3,255,381 | 6/1966 | Tompkins et al. | 324/263 X |
| 4,087,749 | 5/1978 | McCormack | 324/225 |
| 4,482,865 | 11/1984 | George, Jr. | 324/263 |
| 4,594,549 | 6/1986 | Smith et al. | 324/233 X |
| 4,625,167 | 11/1986 | Fitzpatrick | 324/235 |
| 4,706,021 | 11/1987 | Chamuel | 324/242 |
| 4,755,752 | 7/1988 | Fitzpatrick | 324/228 |
| 4,982,158 | 1/1991 | Nakata et al. | 324/263 |
| 5,004,724 | 4/1991 | De | 324/248 |
| 5,053,704 | 10/1991 | Fitzpatrick | 324/235 |
| 5,109,196 | 4/1992 | Wikswo, Jr. | 324/263 |
| 5,258,708 | 11/1993 | Sadeghi et al. | 324/240 |
| 5,293,119 | 3/1994 | Podney | 324/242 |

*Primary Examiner*—Gerard R. Strecker
*Attorney, Agent, or Firm*—Richard V. Westerhoff; Eckert Seamans Cherin & Mellott

[57] ABSTRACT

A sheet inducer carrying a uniformly distributed ac current induces a sheet eddy current generally parallel to a generally smooth surface of an electrically conductive object. A magnetometer, preferably a superconducting quantum interference device (SQUID) magnetometer, detects the component of a magnetic field generally perpendicular to the generally smooth surface resulting from disturbances in the sheet eddy current caused by a flaw. Through appropriate selection of the phase angle between the detector signal and the applied current, the response can be adjusted to suppress surface flaws and enhance detection of flaws below the surface. The sheet eddy current is induced in multiple directions to detect flaws of all orientations and at multiple frequencies to refine determination of the size, shape, and depth of a flaw. An elongated solenoid is used to induce a circumferential sheet eddy current in elongated objects such as tubes and rods, and a current-carrying rod is used to induce a longitudinal sheet eddy current in an elongated tubular object.

22 Claims, 15 Drawing Sheets

FIG.1

FIG.2C
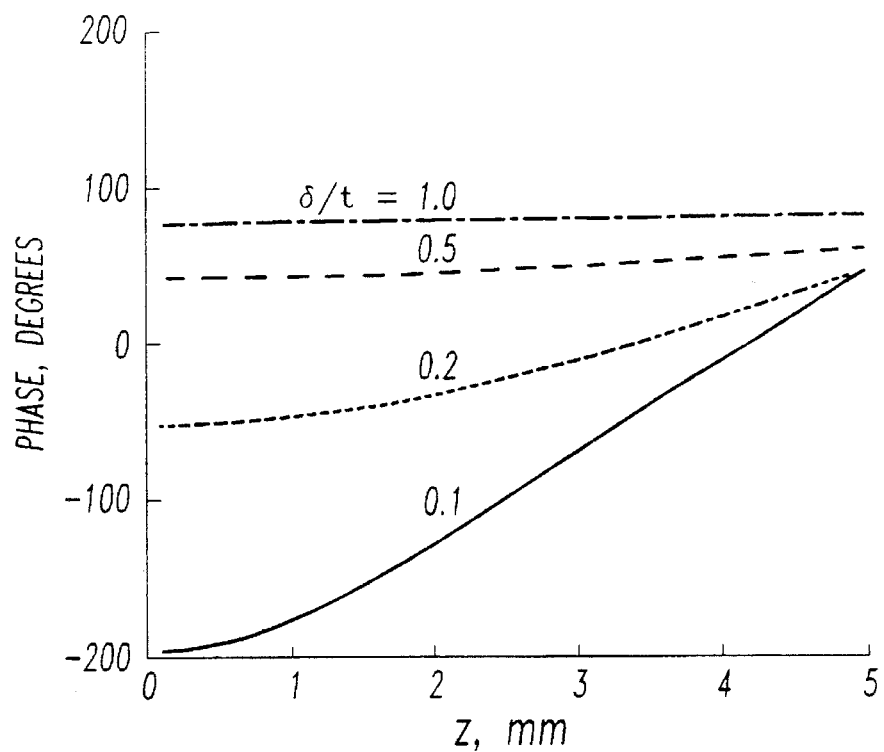
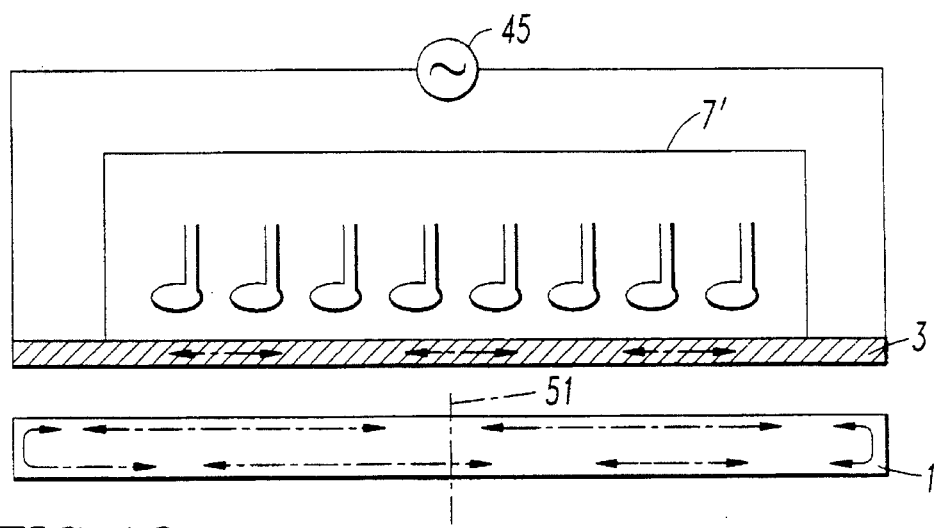
FIG.10

METHOD AND APPARATUS FOR DETECTING FLAWS BELOW THE SURFACE OF AN ELECTRICALLY CONDUCTIVE OBJECT

This invention was made with government support under AFOSR-87-0337 and F 49620-93-0268, awarded by the United States Air Force. The government has certain rights in the invention.

BACKGROUND OF THE INVENTION

1. Field of the Invention

This invention relates to a method and apparatus for low frequency eddy current testing using a magnetometer, and preferably a SQUID magnetometer, to detect flaws on or below the surface of an electrically conductive object.

2. Background Information

Conventional eddy current techniques, which are very sensitive for detecting surface breaking cracks in metal, have been studied and developed extensively for many years. Because of the frequency-dependent skin depth of eddy currents, the detection of deep, non-surface-breaking flaws requires very low frequency eddy currents. However, the key parameters measured by eddy current probes, typically the secondary voltage induced in the pick-up coil or the impedance change of the probe, resulting from eddy currents induced in the conductor by the primary coil, are proportional to the frequency of the magnetic field to be measured. Hence the sensitivity and the signal-to-noise ratio are suppressed drastically at the low frequencies that are required for detection of subsurface cracks. To obtain high sensitivity, most eddy current probes operate at frequencies of tens to hundreds of kilohertz, and the corresponding skin depth in aircraft-grade aluminum alloys varies from 1.2 mm (0.05 in) to 0.2 mm (0.01 in). This is a particularly significant problem in the detection of second and third-layer cracks and corrosion in aging aircraft, and in determining the existence or size of voids in thick soldered assemblies such as splices for electrical generator windings.

As an alternative electromagnetic approach, ac field techniques have been developed during the past decade. Instead of inductively coupling the electromagnetic field above the metal surface as in eddy current methods, the differences in surface electric potential due to a current injected or induced inside the metal are measured by using two electrodes in direct contact with the metal surface. This technique is suitable for a conducting object with a smooth conducting surface, and may be used for dc or low frequency testing. However, the current disturbed by the flaw is constrained largely within a region of comparable dimensions to those of the flaw. A flaw hidden beneath the surface may not disturb the surface potential significantly, even at a low enough frequency, if the distance between the flaw and the surface is larger than the dimensions of the flaw. Thus, the detectability of subsurface flaws is limited.

A modified inducing mechanism for eddy current technique, which consists of two parallel U-shaped wires, has been devised to simplify the complicated calibration procedure in the ordinary eddy current method, but this inductive approach is as yet limited to surface-breaking cracks in ferromagnetic material.

High resolution SQUID (Superconducting Quantum Interference Device) magnetometers, which are very sensitive to dc and low frequency magnetic fields, have been developed and used for detection of flaws in non-ferromagnetic conductors. By injecting a spatially uniform current (dc or low frequency ac current) into a conductor, and measuring the magnetic field normal to the surface, subsurface flaws can be detected. The magnetic field near the surface due to a subsurface flaw is dependent not only on the surface current distribution, as is the case in ac field measurements, but also on the total current disturbed by the flaw inside the conductor.

It is difficult to inject current in several circumstances, such as a conductor covered by an insulation layer, or a cylindrical tube with a crack along the tube axis which requires currents in the azimuthal direction. In these cases, induced eddy currents may be used instead of injected current for SQUID NDE (non-destructive evaluation). In contrast to the eddy current probe, the amplitude of the output signal of the SQUID is independent of the frequency of the field measured, so extremely low frequency (ELF) eddy current measurements are feasible. However, the small excitation coils used in most eddy current techniques induce localized eddy currents circulating inside the conductors, which produce a large magnetic field in the direction normal to the surface. This kind of excitation coil is disadvantageous for a SQUID magnetometer, whose pick-up coil is typically sensitive to the field component normal to the surface, since the magnetic signals due to the current disturbed by flaws in a conductor are difficult to discriminate from the large field background resulting from the large eddy currents circulating beneath the excitation coil.

There is a need therefore, for an improved method and apparatus for detecting sub-surface flaws in electrically conductive objects, including tubular electrically conductive objects.

There is a related need for such a method and apparatus which can detect sub-surface flaws despite the presence of surface flaws.

There is a need for such a method and apparatus which is simple and economical to implement.

SUMMARY OF THE INVENTION

These and other objects are realized by the invention which is directed to a method and apparatus for detecting sub-surface flaws in conducting objects by generating a uniformly distributed current parallel to a generally smooth surface of the electrically conductive object. This uniformly distributed current induces a sheet eddy current in the object parallel to the generally smooth surface. For an extended object without flaws, the magnetic field produced by the sheet eddy current has no component perpendicular to the smooth surface of the object. A flaw in the object produces such a magnetic field component which is detected by a magnetometer, and preferably a SQUID magnetometer. The SQUID magnetometer is ideal for this application as it can measure very small disturbances at the low frequencies of the uniformly distributed current required to induce sheet eddy currents throughout the depth of the electrically conductive object.

For a sinusoidal excitation field, sinusoidal currents will be induced in the test object, but these currents will be phase-shifted with respect to the exciting field. The detector can be made sensitive to magnetic fields at a phase relative to the uniformly distributed ac excitation current selected to detect a flaw at a desired depth below the surface of the electrically conductive object. This phase angle can be selected such that the magnitude of the current density signal at the surface is zero, thereby eliminating the effect of surface flaws which could mask sub-surface flaws using prior art techniques.

Preferably, the in-phase and quadrature components of the detector signal are generated and can be used to generate the magnitude of the secondary field produced by the sheet eddy current for any desired phase angle. In order to assure detection of flaws throughout the depth of the electrically conductive object, uniformly distributed ac excitation currents can be generated at two or more frequencies to induce multi-frequency sheet eddy currents in the object. Detector signals are generated for each frequency and analyzed to determine the magnitude of the response at selected phase angles with respect to the uniformly distributed ac current for each frequency.

In order to preclude the possibility of nondetection of a flaw extending parallel to the sheet eddy current induced in the object, the uniformly distributed ac excitation current can be oriented at two or more orientations with respect to an axis substantially perpendicular to the generally smooth surface. Furthermore, the uniformly distributed ac excitation current can be divided into a number of parallel strips to reduce the effects of eddy currents induced in the induction member by the disturbed currents in the object. When testing electrically conductive objects having a flat, generally smooth surface, a flat induction member, such as a printed circuit board is used to induce the sheet eddy current in the object. For elongated objects with a generally smooth surface, an elongated solenoid is used to induce circumferential sheet eddy currents in the object. A rod induction member can be inserted in a tubular object to induce axial sheet currents to test for circumferentially extending flaws.

BRIEF DESCRIPTION OF THE DRAWINGS

A full understanding of the invention can be gained from the following description of the preferred embodiments when read in conjunction with the accompanying drawings in which:

FIG. 2C is a plot of the phase distribution with respect to the excitation current inside the conducting plate of FIG. 1.

FIGS. 5A–5D are plots of the calculated eddy current at phase angles of 0°, 45°, 85° and 135°, respectively, inside an aluminum plate without a flaw, while

FIG. 10 is a schematic elevation view of a magnetometer array used in practice of the invention and illustrating the positioning of the induction plate between the magnetometer and the sample.

DESCRIPTION OF THE PREFERRED EMBODIMENTS

The invention is directed to detecting flaws in electrically conductive objects by inducing a sheet eddy current in the object generally parallel to a smooth surface of the object, detecting the component of a magnetic field generally perpendicular to the smooth surface of the object resulting from disturbance of the induced eddy current by flaws, including flaws below the surface, and determining the magnitude of this magnetic field component at a phase angle with respect to the current inducing the sheet eddy current selected to detect flaws at a particular depth below the surface.

Figure 1:
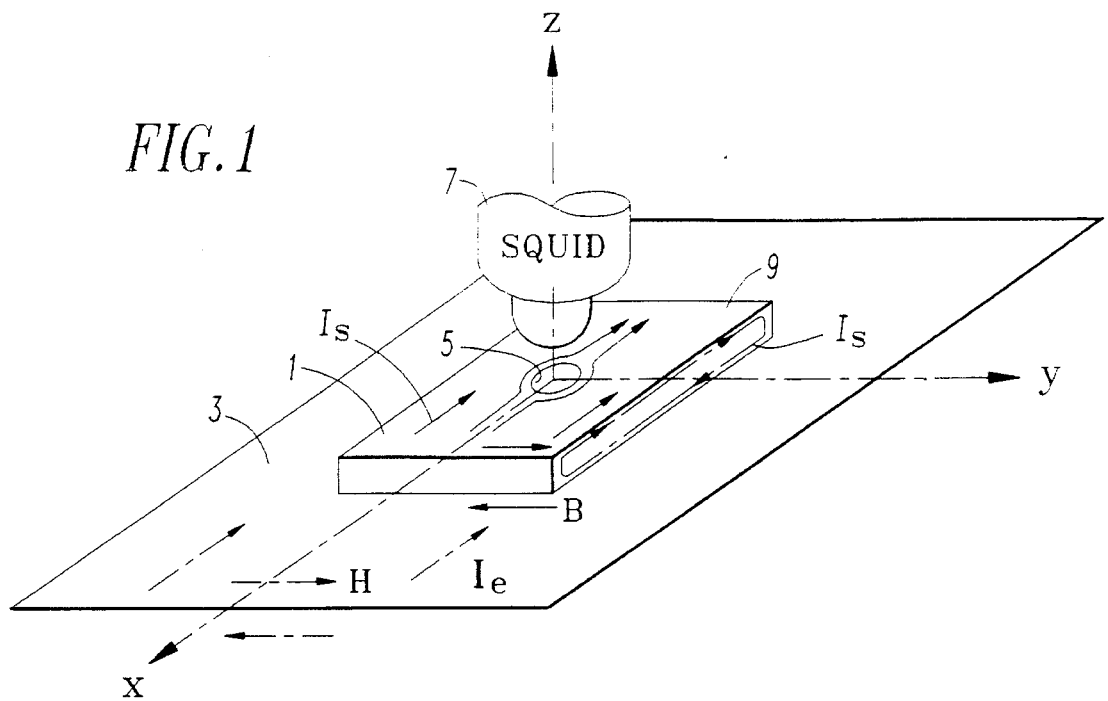
FIG. 1 is an isometric schematic view illustrating the operation of the invention.

FIG. 1 illustrates application of the invention to testing for flaws in a flat conductive plate 1 oriented in an X-Y plane. An induction member 3, in this case, a sheet inducer, is placed adjacent and parallel to the plate 1. A uniformly distributed current $I_e$ flowing in the −X direction is applied to the sheet inducer 3. This current produces a magnetic field H which is parallel to the planes of the sheet inducer 3 and the conductive plate 1 and induces a sheet eddy current $I_e$ which circulates within the plate 1. This sheet eddy current $I_s$ flows parallel to the lower surface of the plate 1 in the +X direction, opposite the current $I_e$, and in the −X direction in the upper surface. Absent any flaws in the conductive plate 1, the sheet eddy current $I_s$ generates a magnetic field B which is parallel to the surfaces of the plate 1 and opposite in direction to the field H. However, the presence of a flaw such as the hole 5 produces a Z component, $B_z$ in the secondary field which can be detected by a magnetometer 7 which is scanned over the surface of the conductive plate 1.

Preferably, the magnetometer 7 is a superconducting quantum interference device (SQUID) magnetometer, which as mentioned, is ideal for detecting the Z component generally perpendicular to the generally smooth surface 9 of the conductive plate 1. It is an advantage of the invention that the sheet eddy current $I_s$ can be induced in the conductive plate 1, and the disturbance of the magnetic field produced by the sheet eddy current $I_s$ by flaws in the conductive plate 1 can be detected by the SQUID detector 7 even if the plate 1 is covered with an electrical insulation or in the presence of other electrical conductivity reducing surface conditions such as corrosion.

The current J induced in the conductive plate 1 is known to be:

$$J_x = \frac{H_o}{\delta} e^{i\omega t}(1+i) \frac{e^{(1+i)z/\delta} - e^{-(1+i)z/\delta}}{e^{(1+i)d/\delta} + e^{-(1+i)d/\delta}} \qquad \text{Eq. (1)}$$

where
$H_o$ equals the magnitude of the induction field
$\omega$ equals $2\pi f$ which is the angular frequency
$\delta$ equals the skin depth or penetration depth per Eq. 2 below
2d equals thickness of the plate This current $J_x$ has both magnitude and phase, relative to the sinusoidal field H, and hence can be described using complex notation, or real and imaginary parts that correspond to the in phase and quadrature components of the current. The skin depth or penetration depth, which depends on the frequency of the external field, H is:

$$\delta = \sqrt{\frac{2}{\omega\mu\sigma}} \qquad \text{Eq. (2)}$$

where
$\mu$ equals magnetic permeability of the plate 1
$\sigma$ equals electrical conductivity of the plate 1

The sheet eddy current $I_s$ density depends on not only the depth, and frequency of the external field, but also the thickness of the plate 1, or the ratio of the thickness to penetration depth. Its distribution is antisymmetric about the center plane of the plate 1.

Figure 2A:
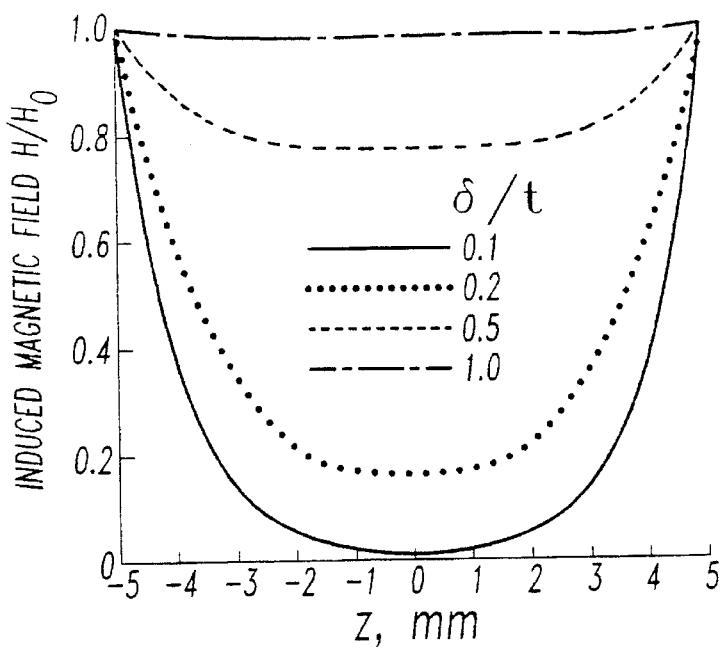
FIG. 2A is a plot of the magnitude of induced magnetic field distribution in the conducting plate of FIG. 1.
Figure 2B:
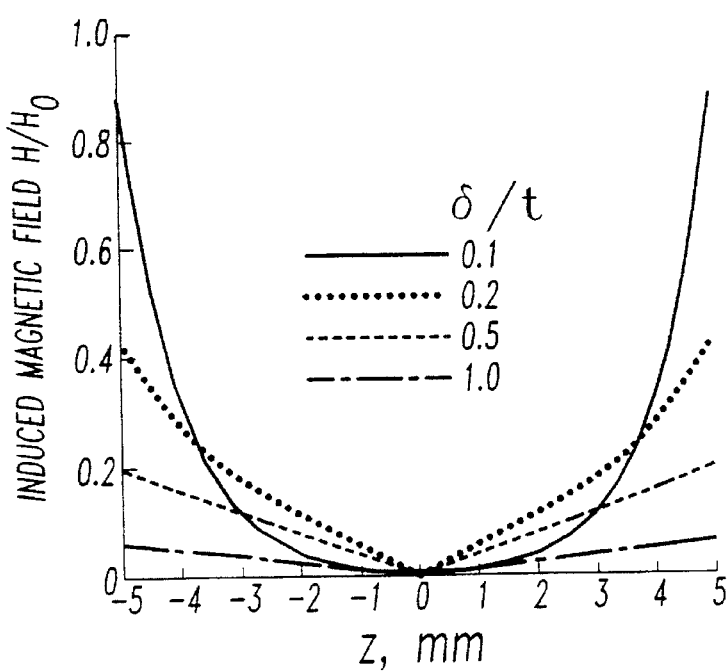
FIG. 2B is a plot of the magnitude of the induced eddy current density distribution inside the conducting plate of FIG. 1 for various ratios of skin depth to thickness.

In principle, an exciting current sheet $I_e$ of infinite extent produces a spatially uniform magnetic field, H, which may induce a sheet eddy current $I_s$ with a well-defined direction inside the conducting plate 1 which is parallel to the current $I_e$. FIG. 2A shows the magnitude of the induced magnetic field distribution (normalized by the external field $H_o$) within the plate 1 and FIG. 2B illustrates the magnitude of the eddy current density distribution, both as a function of z inside the plate 1, calculated using Eq. (1) above for $\delta/t=0.1$, 0.2, 0.5, and 1.0 where $\delta$ is as shown in Eq. (2), and t=2d=10 mm is the thickness of the plate 1. In FIG. 2A, the magnetic fields have been normalized by the external field $H_o$. In FIG. 2B, the current densities are calculated when the excitation current density $I_f=1.0$ mA/mm. As can be seen, at the center of the plate, the current density vanishes, while the magnetic fields remain non-zero in value.

At higher frequencies, where $\delta \leq 0.1t$, both the magnetic field and the current density reduce with depth exponentially within $\delta$ (see the solid line in FIGS. 2A and 2B), which is similar to the case of the semi-infinite extended conductor. However, at lower frequencies, where $\gamma \geq 0.5t$, the induced eddy current density reduces linearly with depth. In the latter case, the actual penetration depth is no longer the same as $\gamma$ given by Eq. (2). In fact, increasing $\gamma/t$, i.e. reducing the frequency, below this point would not increase the real penetration of the induced current into the plate but would simply reduce the magnitude of the eddy current density. At the center plane of the plate, z=0, the current density vanishes, while the magnetic field remains non-zero. The phase of the induced current density relative to the excitation current depends on the depth and ($\gamma/t$), as shown in FIG. 2C, which is for the upper half plate (z>0) only. At z<0, the phase changes by $\pi$ with respect to the phase at z>0.

In practice, the dimensions of the conductor 1 and the conducting sheet 3 carrying the current $I_c$ exciting the eddy current are both finite. To reduce the effect of the edge of the sheet inducer 3, the width of the sheet inducer should be much larger than both the width of the electrically conductive plate 1 and the distance between the sheet inducer 3 and the plate 1.

Figure 3:
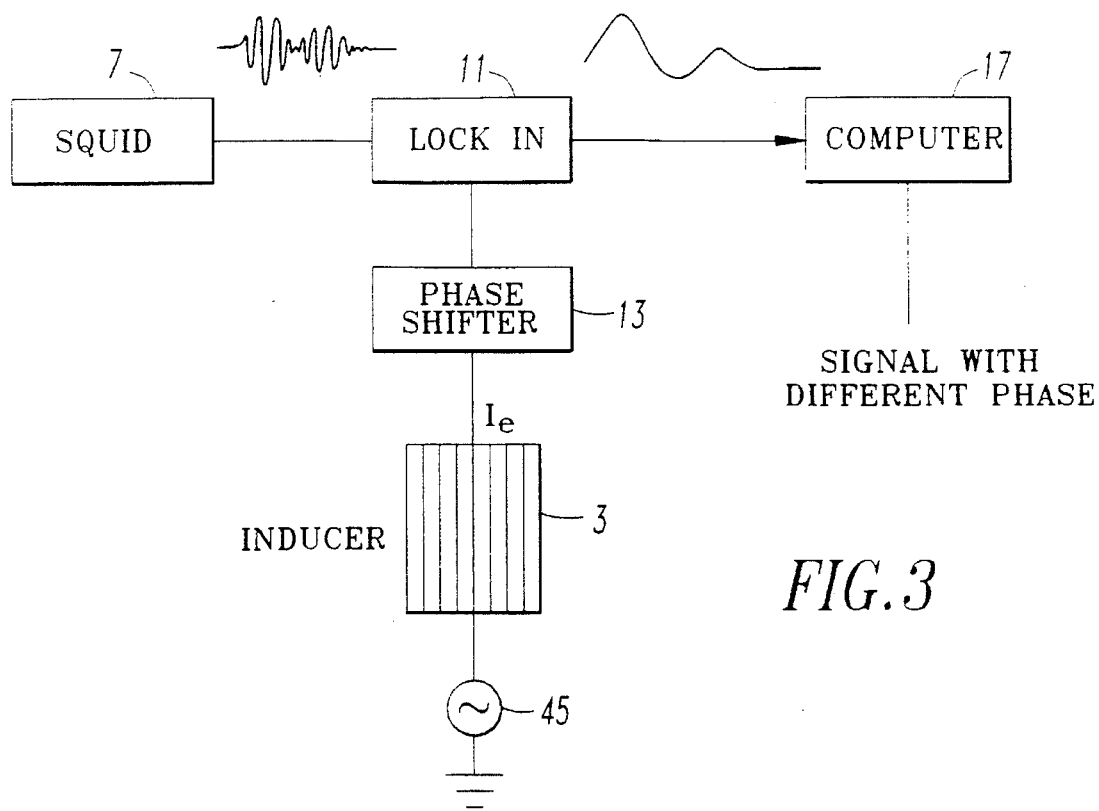
FIG. 3 is a schematic diagram of apparatus in accordance with a first embodiment of the invention for processing signals generated by the setup shown in FIG. 1.

As mentioned above, the SQUID magnetometer 7 detects the z component of the magnetic field produced by disturbances to the sheet eddy current $I_s$ in the conducting plate 1 due to flaws. The SQUID magnetometer 7 is operated as a non-hysteretic, linear device with a bandwidth from dc to about 10 Khz that can record the actual magnetic field waveform. As a result, the SQUID magnetometer 7 can be used in phase sensitive detection schemes that depend upon the relationship between the phase of the current $I_e$ in the sheet inducer 3 and that of the induced currents $I_s$. In such a scheme, the output of the SQUID magnetometer 7 is connected to a lock-in amplifier 11 as shown in FIG. 3, and the applied current $I_e$ waveform is also connected through an adjustable phase-shifter 13 to the reference input of the lock-in amplifier 11 so that SQUID magnetometer 7 output voltage can be measured at a particular phase with respect to the applied current $I_e$. By scanning the SQUID magnetometer 7 over the surface of the sample, or by using an array of SQUIDS, as discussed below, it is possible to obtain an image of the magnetic field at a particular phase angle with respect to the applied current. By selecting this phase properly, as will be shown below, it is possible to make this measurement system preferentially sensitive to flaws at a particular depth beneath the surface 9 of the conducting plate 1, or to make the system insensitive to flaws on the surface.

Figure 4:
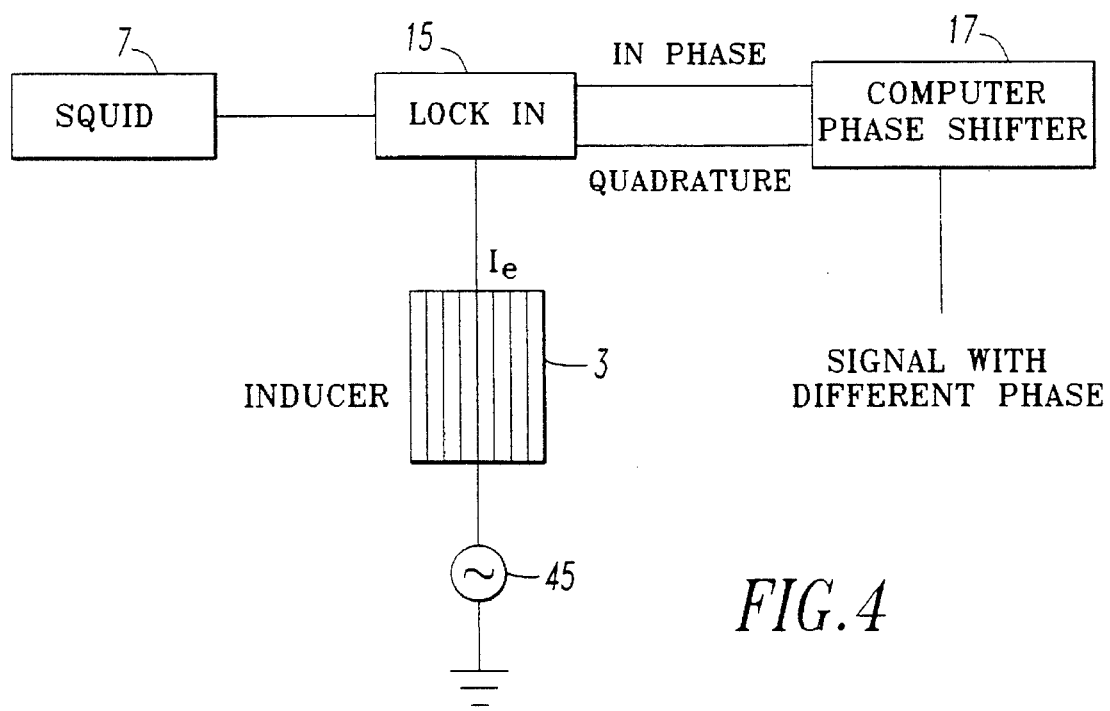
FIG. 4 is a schematic diagram of apparatus in accordance with a second embodiment of the invention for processing the signals generated by the setup of FIG. 1.

One disadvantage of the arrangement shown in FIG. 3 is that a separate image has to be recorded at each phase angle. If instead, a two-phase lock-in amplifier 15 is used, as shown in FIG. 4, and the in-phase image $B_1(xy)$ and the quadrature image $B_Q(xy)$ are both recorded at every point (xy) in the digitized image, a numerical algorithm can be used to compute the image at any desired phase angle $\phi$, given by:

$$B_\phi(x,y) = (x,y)\cos\phi + B_Q(x,y)\sin\phi \qquad \text{Eq. (3)}$$

The choice of $\phi$ can be made either empirically to enhance the image, or as will be shown, it can be determined theoretically given the conductivity of the sample and the desired measurement frequency.

It is well known that the magnitude of the eddy current density reduces monotonically with depth toward the center of the plate, as shown in FIG. 2B. However, the current density at a specific phase angle with respect to the excitation current will exhibit a more complicated behavior. For example, the calculated eddy currents at phase angles $\phi$ of 0°, 45°, 85°, and 135° inside a 12.6 mm thick aluminum plate without flaw are shown in FIGS. 5A–5D, where the excitation current density is 0.1 mA/mm. A skin depth $\delta$ of 2.4 mm was used for this calculation, which implies that the frequency of the excitation current is about 2.5 KHz for 7075 aluminum alloy. The vertical axis is the induced eddy current density with units of ma/mm².

Figure 5A:
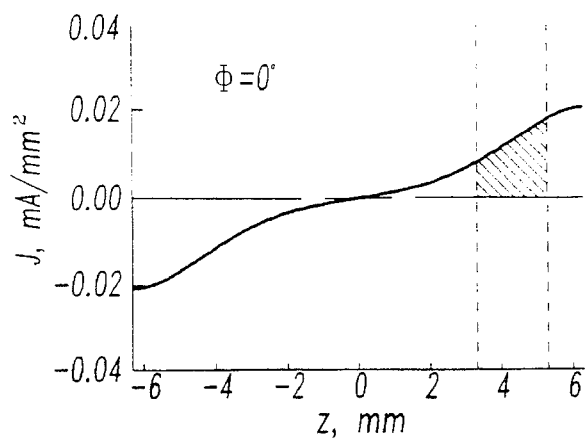

FIG. 5A shows that the in-phase component is positive on the upper surface of the plate (z=6.3 mm), with an amplitude that reduces to zero at the center of the plate, and then changes polarity. At $\phi=45°$ in FIG. 5B, the value of induced current density at the surface becomes larger, and then reduces to zero at 4 mm below the surface. At $\phi=85°$ in FIG. 5C, the positive current density at the surface becomes smaller, while the negative current density beneath the surface becomes larger, and reaches a maximum value at 3 mm below the surface. At $\phi=135°$, as shown as in the FIG. 5D, the current density at the surface of the plate becomes zero, while the current beneath the surface essentially penetrates through the whole plate with a local null at the center plane of the plate. The ability to control the depth at which the current density becomes relatively larger is a potentially useful means to adjust depth sensitivity and to search preferentially for non-surface breaking flaws.

Figure 5B:
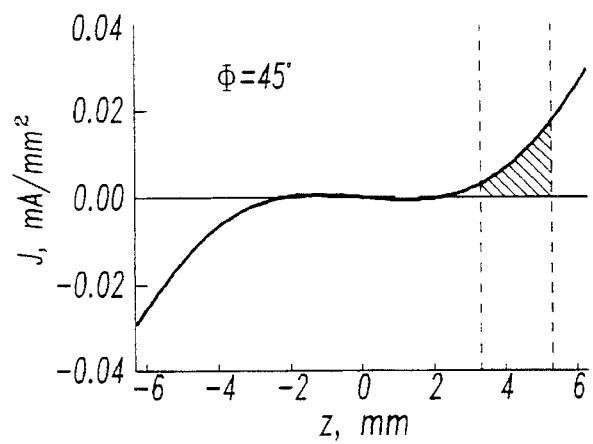
Figure 5C:
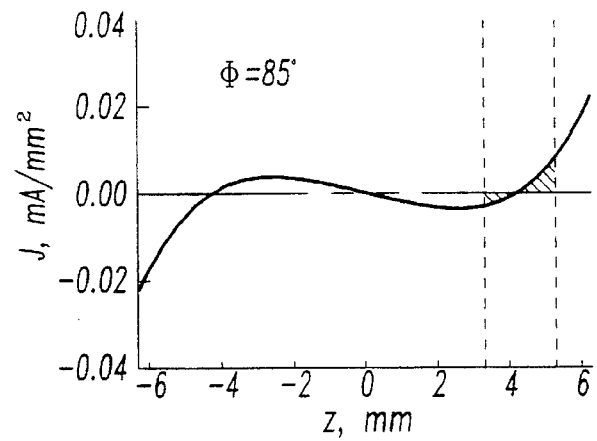
Figure 5D:
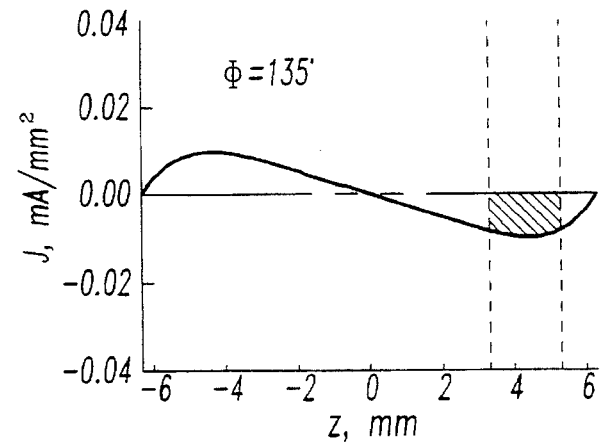
Figure 5E:
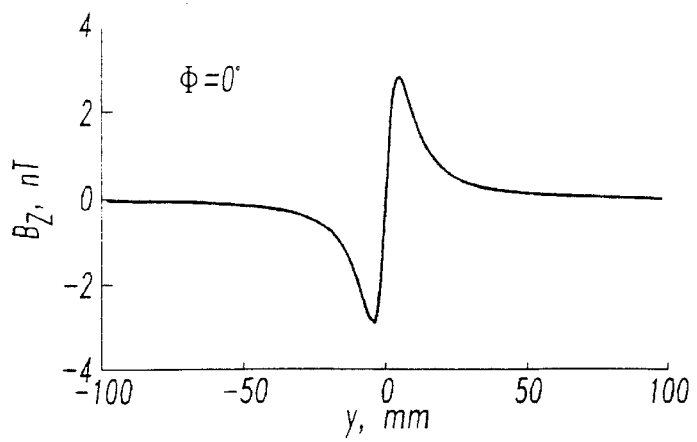
FIGS. 5E–5H are plots of the simulated magnetic signal at the phase angle shown in FIGS. 5A–5D due to a void below the surface of the plate.
Figure 5F:
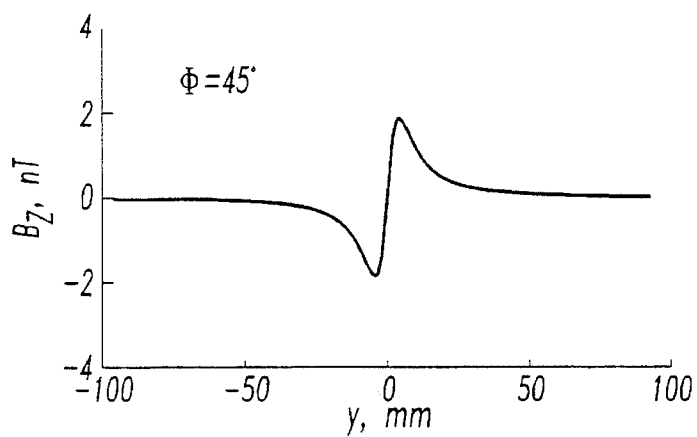
Figure 5G:
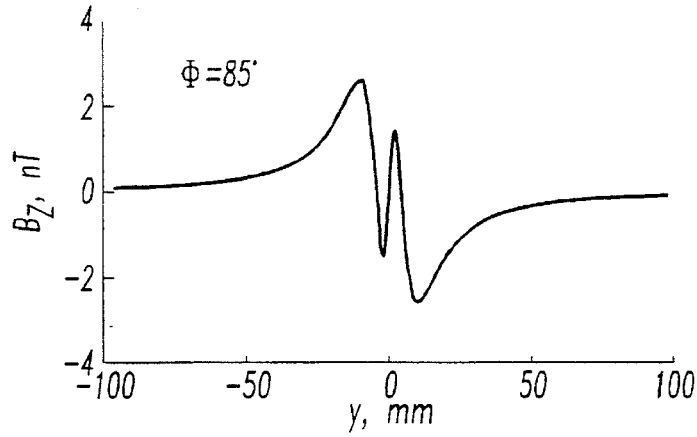
Figure 5H:
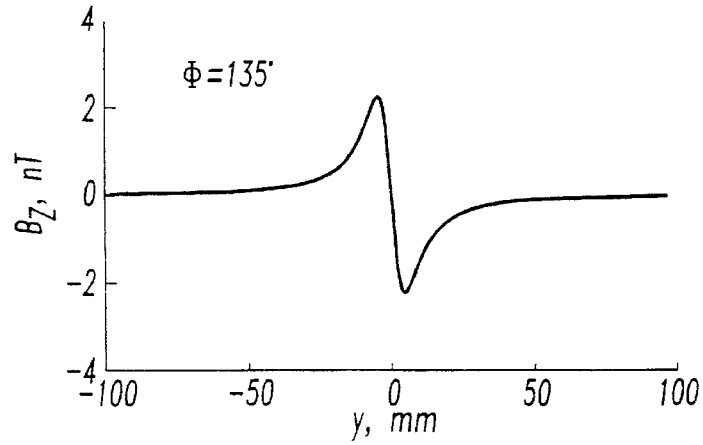

To examine how the depth dependence of the current at a particular phase angle affects the magnetic signature of a flaw, we will first consider a cylindrical void (i.e., zero conductivity) that is 8 mm in diameter and 3 mm tall, and whose upper end is 1 mm below the surface of the plate. The current densities distributed by the void are shown by the shaded areas in FIGS. 5A–5D, where the dotted lines indicate the location of the cylinder ends. FIGS. 5E–5F show the simulated magnetic signal at 3 mm above the surface of the plate due to the void at the phase angles $\phi=0°$, 45°, 85° and 135° as determined by the current densities shown in FIGS. 5A–5D, respectively. The dipolar signals in FIGS. 5A and 5B are primarily the result of the large positive current near the surface. FIG. 5C, where $\phi=85°$, shows that the negative subsurface current within the depth of the void becomes comparable with the positive current near the surface, which produces an additional biphasic signal with opposite polarity but with a different peak-to-peak spacing. Thus, the dipolar signal splits to one with four extrema (quadrupolar), as shown in FIG. 5G, that is noticeably different from the simple diphasic signal obtained by injecting a dc current. Obviously the sharper peak is due to the positive current near the surface. At $\phi=135°$, the quadrupolar signal becomes a dipolar signal again (FIG. 5F), with reversed polarity due to the negative current density below the surface (see FIG. 5D).

For the qualitative analysis of flaw signals, there are two important parameters: the amplitude of the signal and the separation between its minimum and the maximum. In the case of an injected dc current, the amplitude of the magnetic signal, which is proportional to the current density, increases with the size of the flaw and depends on the orientation of the flaw with respect to the current. The separation between the maximum and minimum of the dipole signal is equal to $\sqrt{2} z_o$, where $z_o$ is the distance between the flaw and the sensor, which is valid only if the flaw is much smaller than $z_o$. When one or more dimensions of the flaw are much larger than $z_o$, the separation of the two peaks can also depend on the shape and dimensions of the flaw.

In the case of an induced eddy current, the current density distribution is a function of both depth and phase, so that the qualitative analysis of the magnetic signal becomes more complicated. The amplitude of the dipolar signals in FIGS. 5E–5H changes with the phase, and depends on the value of the shaded area in FIGS. 5A–5D, respectively. As a consequence, the phase at which the quadrupolar signal appears and disappears (transition region) for a fixed frequency depends upon the depth and geometry of the flaw. In addition, the separation between the maximum and the minimum varies with the phase.

As an example, we have calculated the phase-related amplitude (taken from the larger peak for the quadrupolar signal) and the separation between the maximum and minimum of the magnetic signals from slots with various dimensions at several locations in a 12.6 mm thick aluminum plate. We chose an excitation current density of 0.1 A/m, and a standard penetration depth of 2.4 mm, which implies a frequency of 2.5 KHz for 7075 aluminum alloy.

Figure 6A:
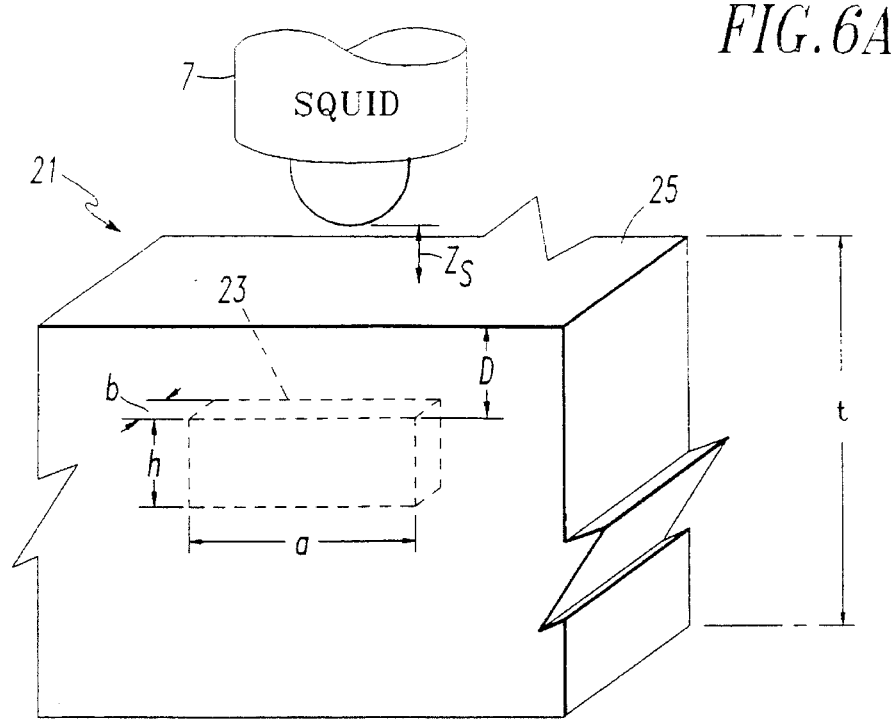
FIGS. 6A–6D illustrate respectively, a set-up for calculation of magnetic signals generated by a void at various depths below the surface of a conducting plate, the calculated amplitude of the magnetic signal due to the void as a function of phase angle, the separation between the maximum and minimum value of the signal as a function of phase angle, and the calculated square of the magnetic signal as a function of phase angle.

FIG. 6A illustrates a 12.6 mm thick plate 21 having a slot 23 of length a, width b and height h and a depth D below the upper surface 25. The height of the SQUID 7 above the upper surface 25 is $z_s$. The dimensions and the location of the slot 23 used for calculation are listed in Table I.

TABLE I

| line | a (mm) | b (mm) | h (mm) | D (mm) | $\phi_{min}$ | $S_{pp}$ (mm) | $W_{tr}$ (mm) |
|---|---|---|---|---|---|---|---|
| solid | 4 | 0.2 | 1 | 0 | 121° | 5.4 | <1° |
| dotted | 4 | 0.2 | 1 | 1 | 99° | 6.8 | <1° |
| dashed | 4 | 0.2 | 1 | 2 | 75° | 8.0 | <1° |

Figure 6B:
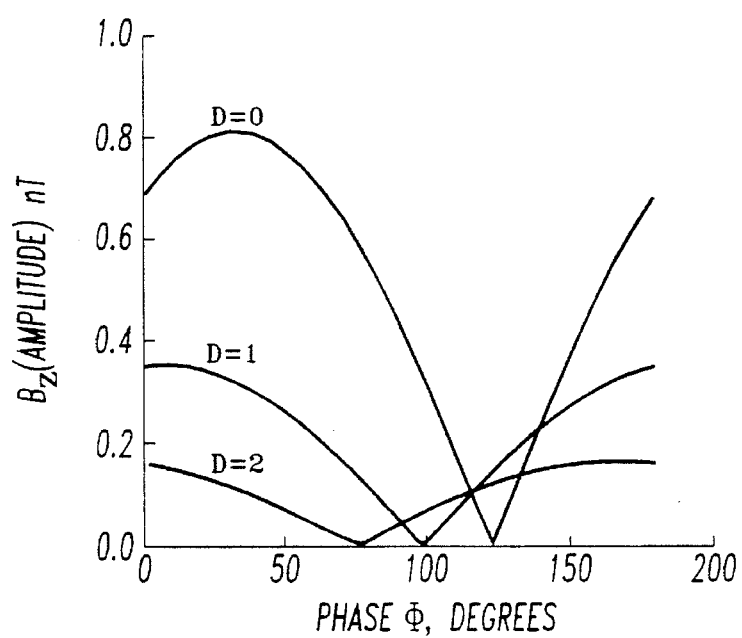

FIG. 6B shows the amplitude of the signal for the slots at D=0 (solid line), D=1 mm (dotted line), and D=2 mm (dashed line). The amplitude is minimum at a phase angle ($\phi_{min}$) of 121° for the slot at D=0, 99° for the slot at D=1 mm, and 75° for the slot at D=2 min. At most phase angles, the amplitude of the signal due to the surface breaking slot (D=0 mm) is larger than those due to the subsurface slots. However, between $\phi=115°$ and 140°, the subsurface slots produce larger signals than does the surface slot, demonstrating that this technique is useful for enhancing the signal due to subsurface flaws and reducing the background signal due to surface structures.

Figure 6C:
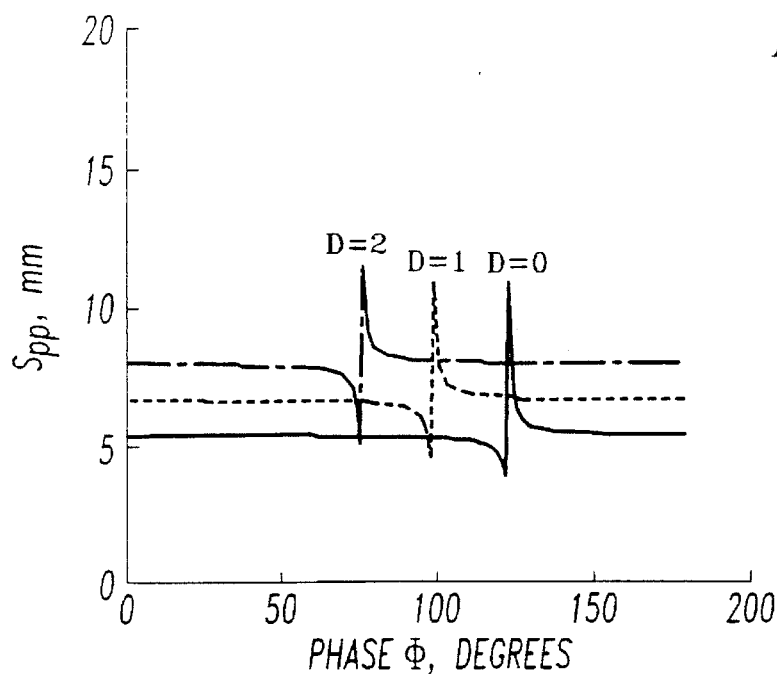
Figure 6D:
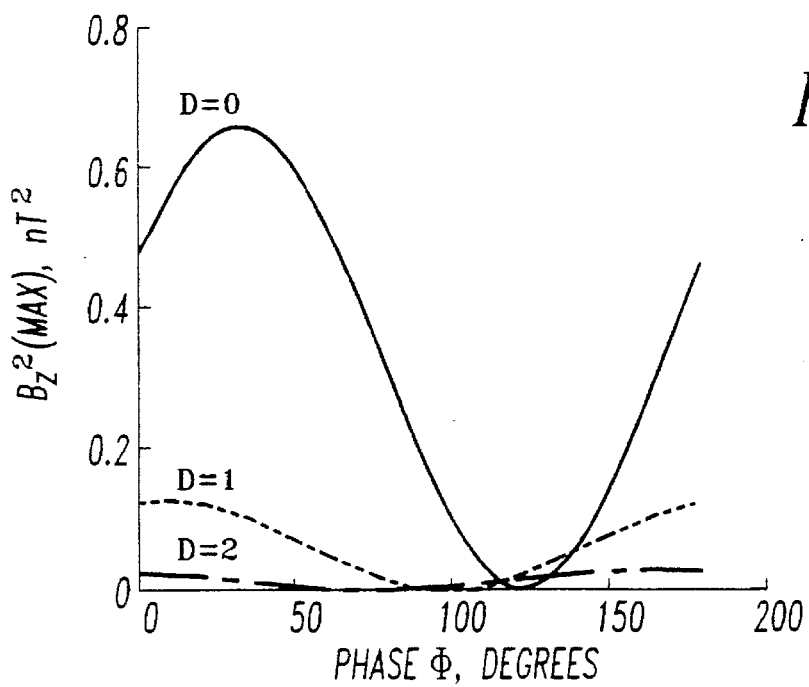

The baseline value of the separation between the maximum and the minimum of the signal ($S_{pp}$, as shown in FIG. 6C, is 5.4 mm, 6.8 mm and 8 mm for the slots at D=0 mm, 1 mm, and 2 mm, respectively (See Table I). At the transition region, within which the quadrupolar signal appears and disappears, the separation between the maximum and the minimum decreases and then rapidly increases to the largest value. The width of the transition region ($W_{tr}$) is less than 1° for all three slots, and hence is not strongly dependent upon the location of the flaw below the surface (see FIG. 6C). FIG. 6D shows the maximum of squared magnitude $B_z(max)$, which is a cosine function of phase $\phi$.

Figure 7A:
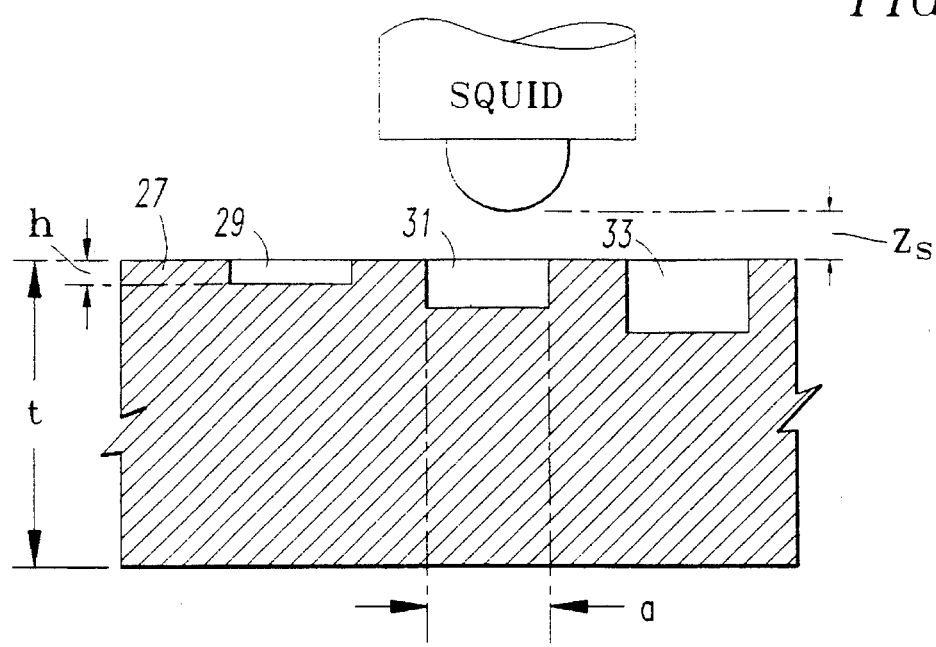
FIGS. 7A–D illustrate respectively, an arrangement for calculating the magnitude of the magnetic signals caused by surface voids of varying depth in a conducting plate, the calculated value of the magnetic signal as a function of phase angle for the various depths of the void, the maximum and minimum values of the magnetic signal as a function of phase angle, and the square of the magnetic signal as a function of phase angle.

FIG. 7A illustrates a 12.6 mm thick plate 27 having slots 29, 31 and 33, all at the upper surface 35 (D=0), and having a length a, width b and a height h, where the height h is 1 mm, 2 mm and 3 mm, respectively. The calculations for these slots are set forth in Table II.

TABLE II

| line | a (mm) | b (mm) | h (mm) | D (mm) | $\phi_{min}$ | $S_{pp}$ (mm) | $W_{tr}$ (mm) |
|---|---|---|---|---|---|---|---|
| solid | 4 | 0.2 | 1 | 0 | 122° | 5.4 | <1° |
| dotted | 4 | 0.2 | 2 | 0 | 115° | 5.8 | 6° |
| dashed | 4 | 0.2 | 3 | 0 | 110° | 6.0 | 10° |

Figure 7B:
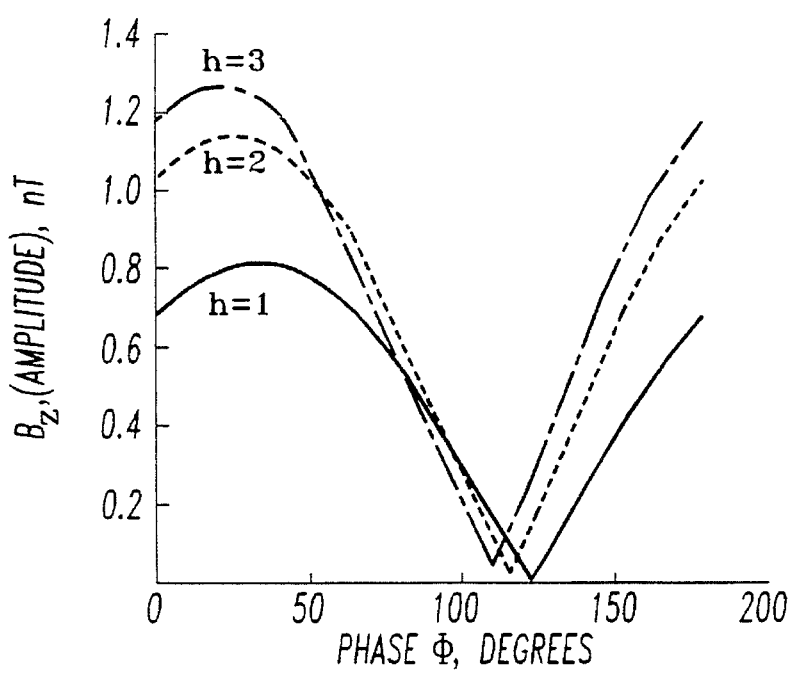
Figure 7C:
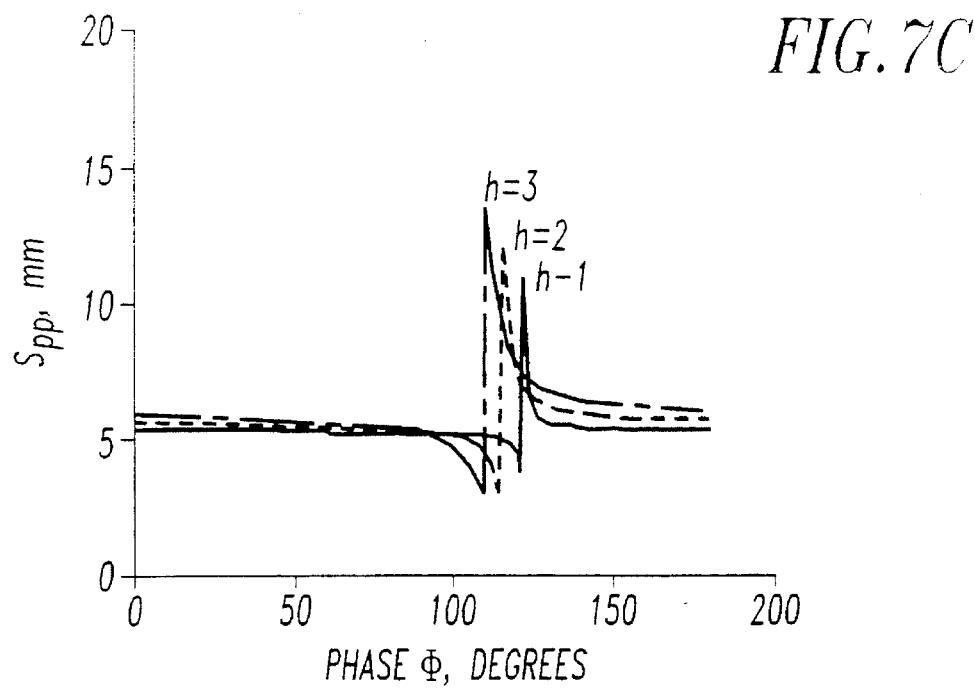
Figure 7D:
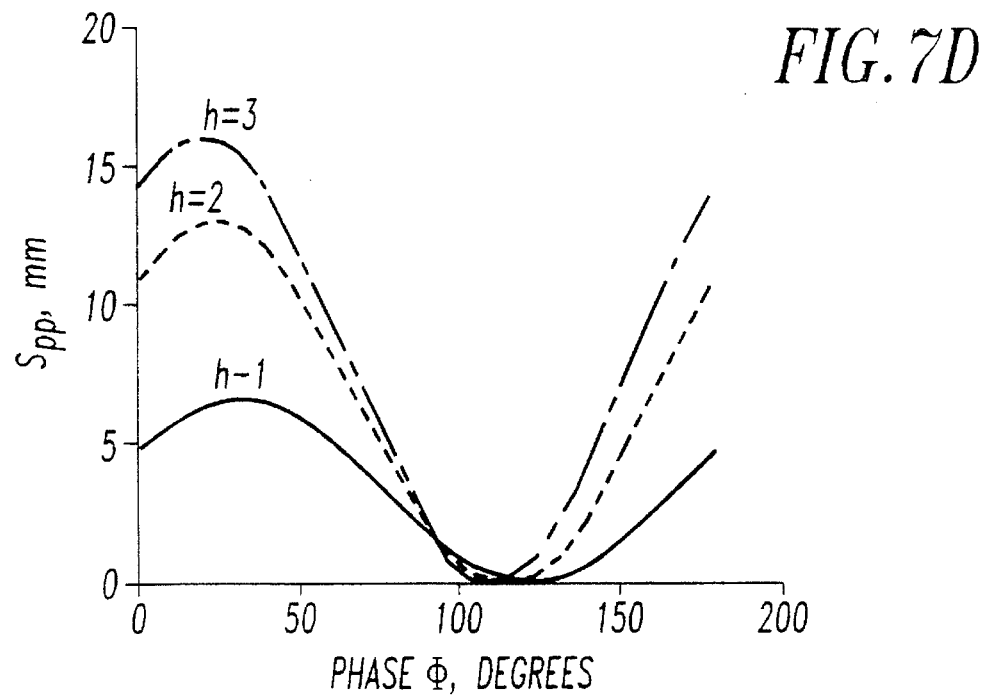

FIG. 7B shows the amplitude, 7D the amplitude of the squared signal, and 7C the separation between the maximum and the minimum for the surface breaking slots with h=1 mm (solid line), 2 mm (dotted line), and 3 mm (dashed line)

for the slots 29, 31 and 33 respectively. The phase at which the amplitude becomes minimum ($\phi_{min}$) is 122°, 115° and 110° for the slots with vertical height, h, of 1 mm, 2 mm and 3 mm, respectively (see FIG. 7B). It is clear that the transition region is much wider for the slots with greater vertical height, shown as in FIG. 7C, where the transition region is <1°, 6°, and 10° for the slots with h=1 mm, 2 mm, and 3 mm, respectively (see Table II).

Comparing Table I with Table II, we see that the phase at which the amplitude becomes minimum (or maximum) ($\phi_{min}$) is determined by the depth of the flaw below the surface (D), while the width of the transition region ($W_{tr}$) is determined by the vertical height of the flaw (h). Both of them depend on the parameter $\gamma/t$, which is the function of frequency for a particular material. These phase-related features provide a potential method to determine the depth and the extent of the flaw.

Because the phase of the eddy current changes more at higher frequencies, shown as in FIG. 2C, it is better to use as high a frequency as possible for the phase analysis. Since the amplitude of the signal for the deeper flaw is reduced more at higher frequencies, it is necessary to determine an optimum frequency for a particular measurement or to use multiple frequencies. In general, the optimum value for $\gamma/t$ is between 0.1 and 0.5.

Figure 8A:
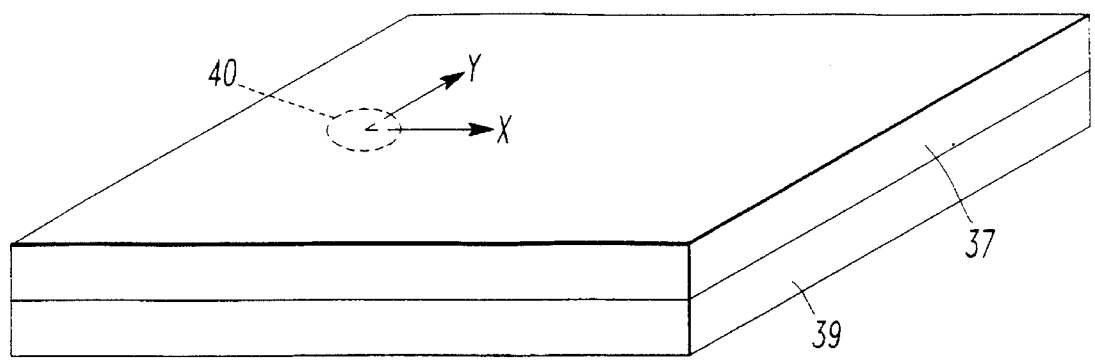
FIGS. 8A–G show respectively: an isometric view of a test sample comprising two electrically conductive panels, a cross section of the panels showing a void in the upper surface of the lower panel, a contour plot of the magnetic signals generated by that void, a plot of the magnetic signal as a function of phase angle, a cross-sectional view through the plates wherein the void is in the lower surface of the upper panel, a contour diagram of the magnetic signal produced by that void, and a plot of the magnetic signal for that void as a function of phase angle.

We have used this approach to detect hidden corrosion in the second layer of a simulated aircraft lap joint. As shown in FIG. 8A, the sample consisted of two 100×125 mm by 4.1 mm thick 7075-T6 aluminum panels 37, 39 bonded together with sealant. The exterior surfaces were painted with epoxy and polyurethane enamel. The hidden corrosion area 40, 9.5 mm in diameter, was in one of the surfaces between the two panels, as shown as FIGS. 8B and 8E, and the corrosion depth was measured as 7% of the thickness of one panel of the sample. Because the exterior surface was not conducting, it was not possible to inject current into the sample. The sheet inducer 3 carrying a 7.7 mA, 5 KHz ($\gamma \approx 1.7$ mm) current was placed beneath the sample to induce an eddy current in the x direction.

Figure 8B:
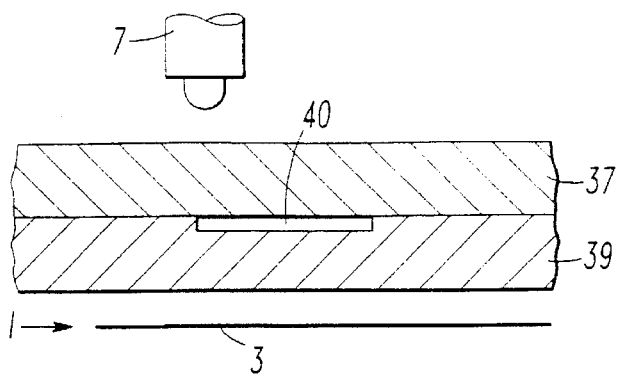
Figure 8C:
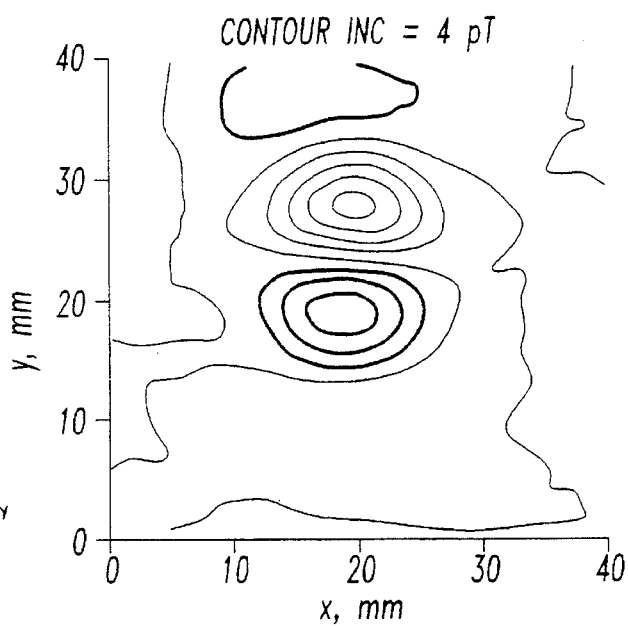
Figure 8D:
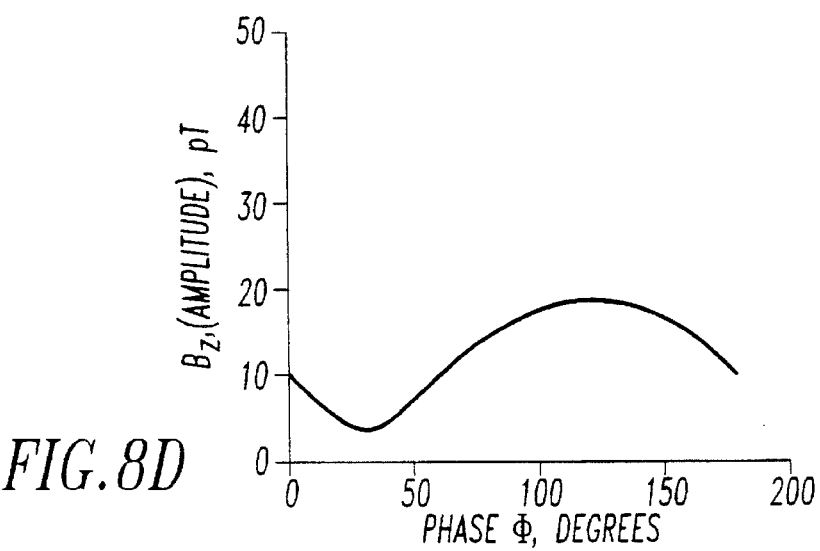
Figure 8E:
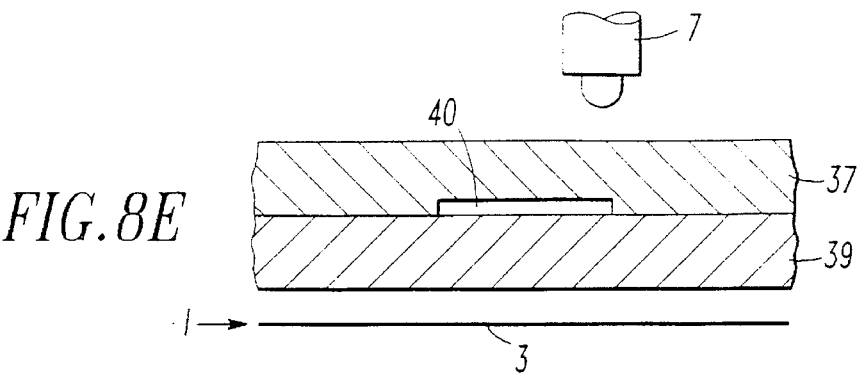
Figure 8F:
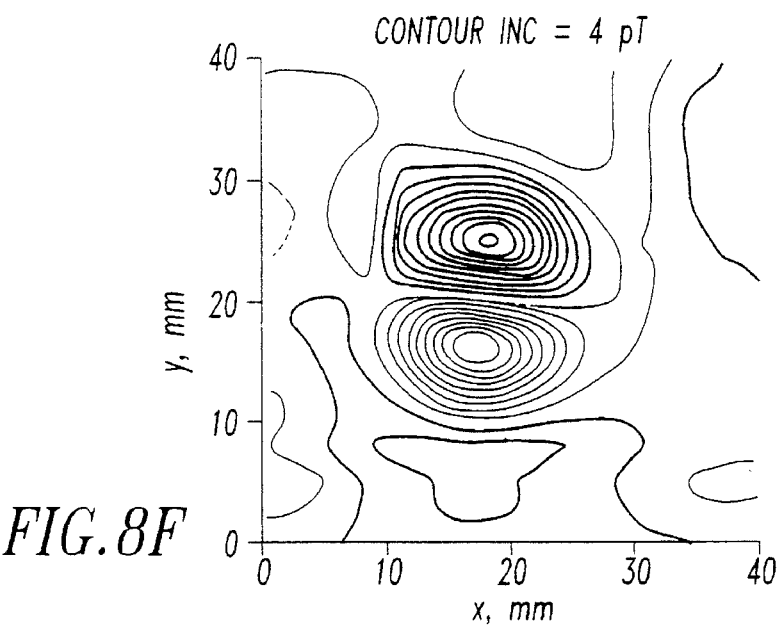

FIG. 8C is the field contour map when the corroded area 40 was in the upper surface of the lower plate (see FIG. 8B), while FIG. 8F is the contour map for the corroded area 40' in the lower surface of the upper plate and closer to the SQUID 7 (see FIG. 8E). Both contour maps were taken at a phase of 100°, and the contour interval is 4 pT. FIGS. 8C and 8F show the amplitude of the signal as a function of phase angle for sample orientations (b) and (e), respectively.

Figure 8G:
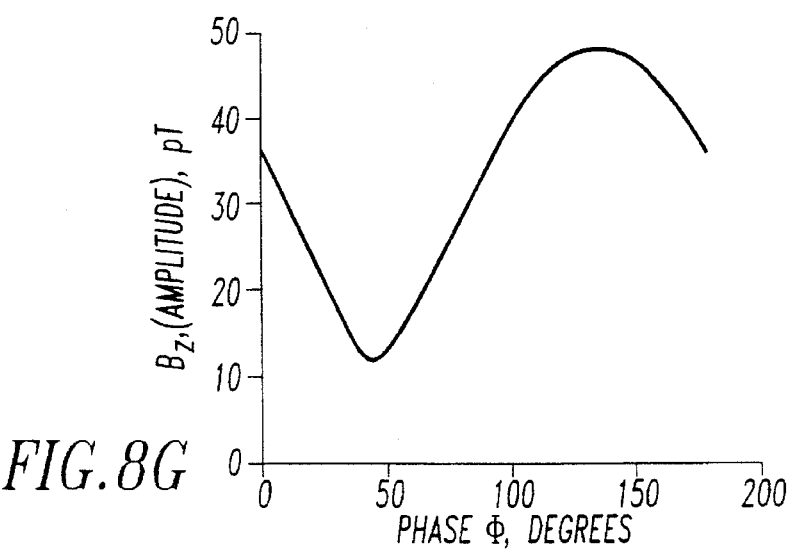

The amplitude of the signal in FIG. 8D is less than one-half of that in FIG. 8G. The corrosion in the lower panel is approximately 1 mm deeper than the corrosion in the upper panel, which would result in the signal from the lower panel being reduced by a factor of 0.85 relative to the upper one, rather than the observed factor of 0.5. The other contribution to the reduction of the signal is believed due to the mutual inductance between the two panels 37, 39 which are insulated from each other: the magnetic field due to the corrosion in the lower panel was partially shielded by the upper, unflawed panel.

There is an approximately 10° phase shift between the signal due to the lower-layer corrosion and the signal due to the upper layer corrosion. Obviously, the polarity of the signal in FIG. 8C is opposite to that of the signal in FIG. 11F, because one is in the upper surface of the lower panel (FIG. 8C) and the other is in the lower surface of the upper panel (see FIG. 8F), for which the eddy current flows in the opposite direction.

Figure 9:
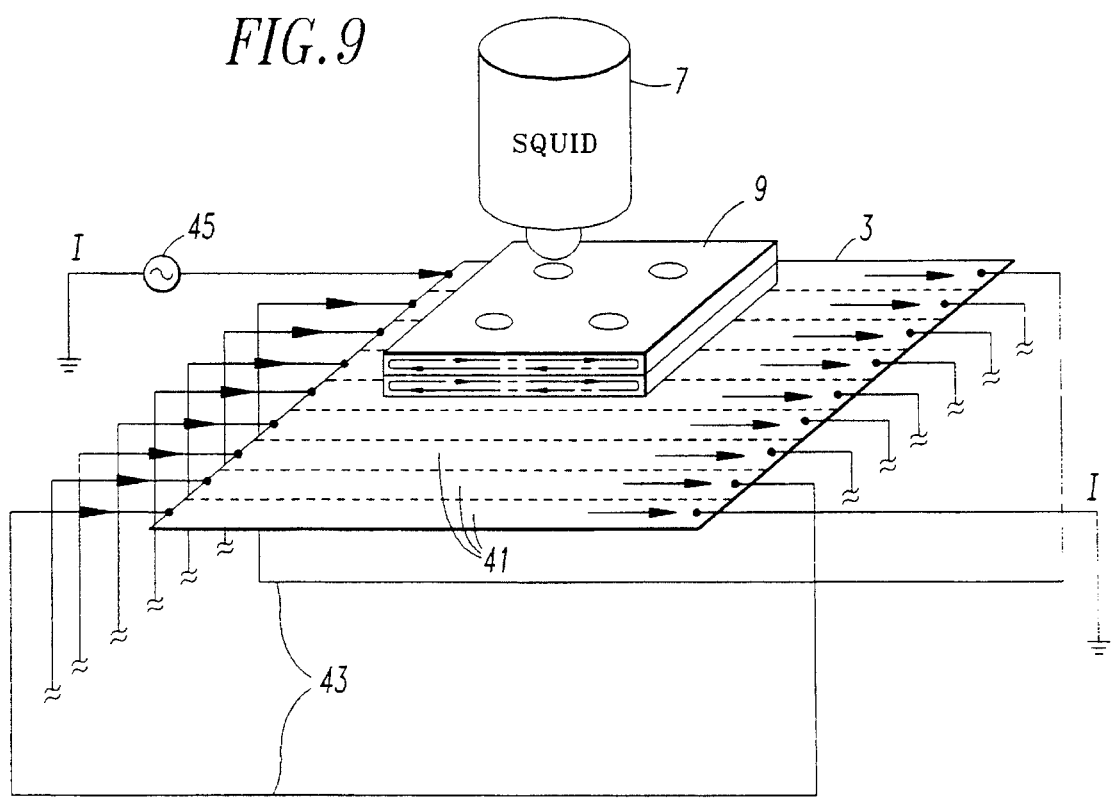
FIG. 9 is a schematic isometric view of a striped induction member in accordance with the invention.

In order to minimize the effects of eddy currents induced in the sheet inducer 3 by the disturbances in the induced sheet eddy currents $I_s$ resulting from flaws in the conducting object, the sheet inducer 3 can be, as shown in FIG. 9, divided into parallel strips 41, each about 2 cm wide, which are connected in series by leads 43 to an ac source 45.

While the electrically conductive objects 1 and 37, 39 are shown in FIGS. 1 and 8B, and E, as being placed between the SQUID and the induction member 3, it is preferred that the induction member 3 be placed between the SQUID and the electrically conducting object 1 as shown in FIG. 10. This does not interfere with the location of the SQUID in close proximity to the conducting object 1 since as mentioned above, the induction member 3 can be a film on a printed circuit board. In order to enhance detection of a flaw which may be parallel to the sheet eddy current $I_8$, it is preferred that magnetometer measurements be made at more than one orientation of the sheet eddy current with respect to the object 1. At least two sets of measurements with the sheet eddy current oriented in two orthogonal directions should be taken. It is also preferred that an array of SQUIDs 7', which may be linear or two dimensional, be used to reduce measurement time.

Figure 11:
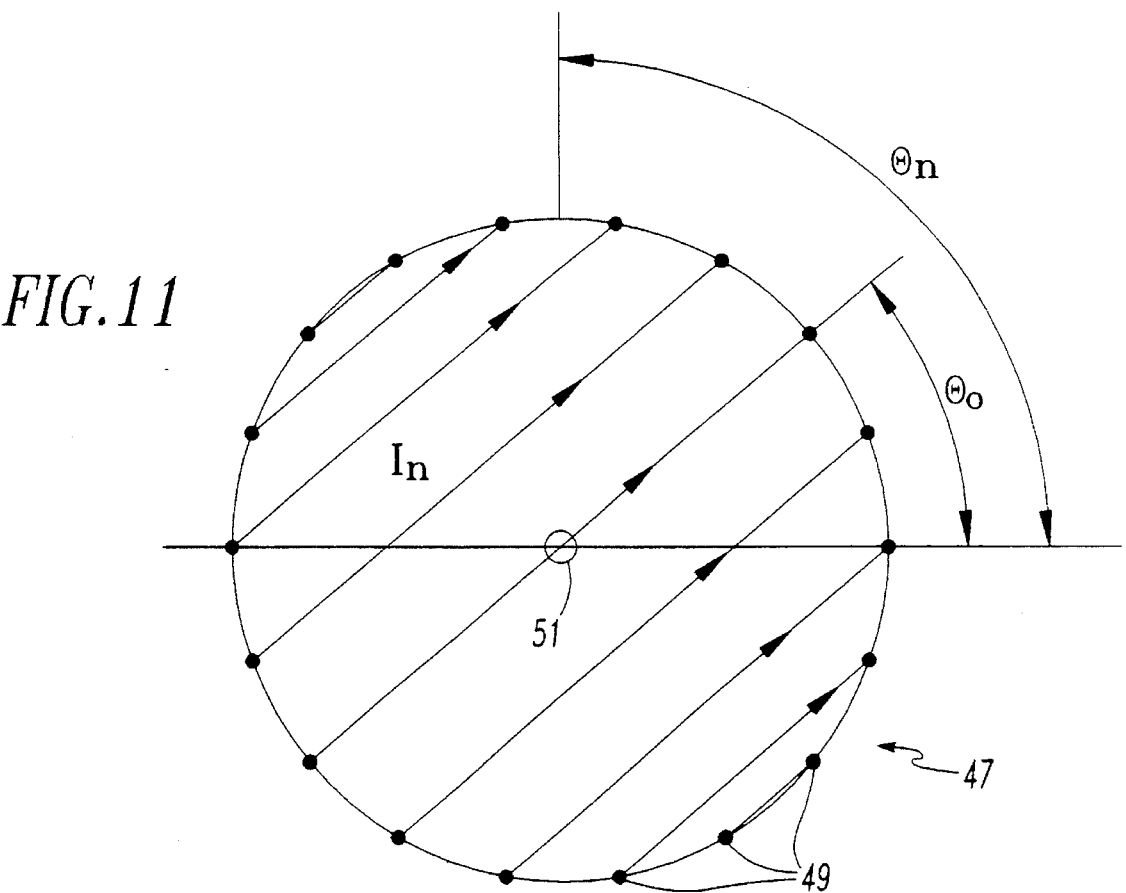
FIG. 11 is a plan view of a circular induction member in accordance with the invention showing how the orientation of the current can be rotated.

The analysis we have presented so far assumes that the induced currents flow in a single direction in the inducer, and that the analysis of the data will be performed at only a single frequency. If we relax these assumptions, it is possible to extend this approach to allow three-dimensional tomographic reconstruction of the conducting object. It is known that the magnetic signature of an elliptical flaw depends upon the direction of the applied current relative to the axis of the flaw. However, the current can be applied from multiple directions, to allow determination of the shape of the flaw. As shown in FIG. 11, this can be done by either rotating the inducer 47, or by using a circular inducer with multiple wires 49, connected to the periphery of the plate, each of which carries a current given by $I_n = I_o \cos(\theta_o - \theta_n)$, where $\theta$ is the desired angle of the uniform current in the inducer and $\theta_n$ is the angle of the $n^{th}$ wire measured about a central axis 51 perpendicular to the circular inducer 47. Sequential measurements would simply be made with different values of $\theta_o$. Other current distributions could also be produced if desired. In electrical impedance tomography, this approach is used, but instead of imaging the current distribution between various combinations of electrodes, only the potential drops between all electrode pairs are recorded. With SQUID current tomography, the magnetic field from each current configuration would be imaged over the entire surface of the object. While this problem is ill conditioned, it should be more stable than the electric tomography: for a two dimensional current distribution, the magnetic problem has a unique solution that provides an image of the currents in the plane, rather than requiring a self-consistent calculation of the overall current distribution throughout the plate given only the potentials at the edge.

In the case of thick samples, the magnetic and electric tomography problems become more complex, but the eddy current/phase shift technique should provide a new approach. As we described in detail above, the choice of phase angle in the image determines the depth at which the zero-current plane occurs. While one might think that it would be possible to sweep the phase angle so as to obtain an image across the depth, it is important to realize that at each measurement point only two numbers are recorded: the in-phase and quadrature components of the magnetic field. Thus, in an overly simplistic way, it follows that the sample could at most be divided vertically into only two zones—one above a chosen zero crossing and one below, so that if the image had N pixels, the three-dimensional current reconstruction might have 2N voxels, although it may be prudent to use singular value decomposition and obtain a more stable inverse with fewer than 2N voxels. However, because the eddy current approach could be used at M different frequencies, it may be possible, if adequate frequency separation is achieved to make 2M vertical separations, or a three dimensional current reconstruction with 2M·N voxels. Of course, more sophisticated analysis of the magnetic images could also contribute depth information in a model-dependent inverse solution.

Figure 12:
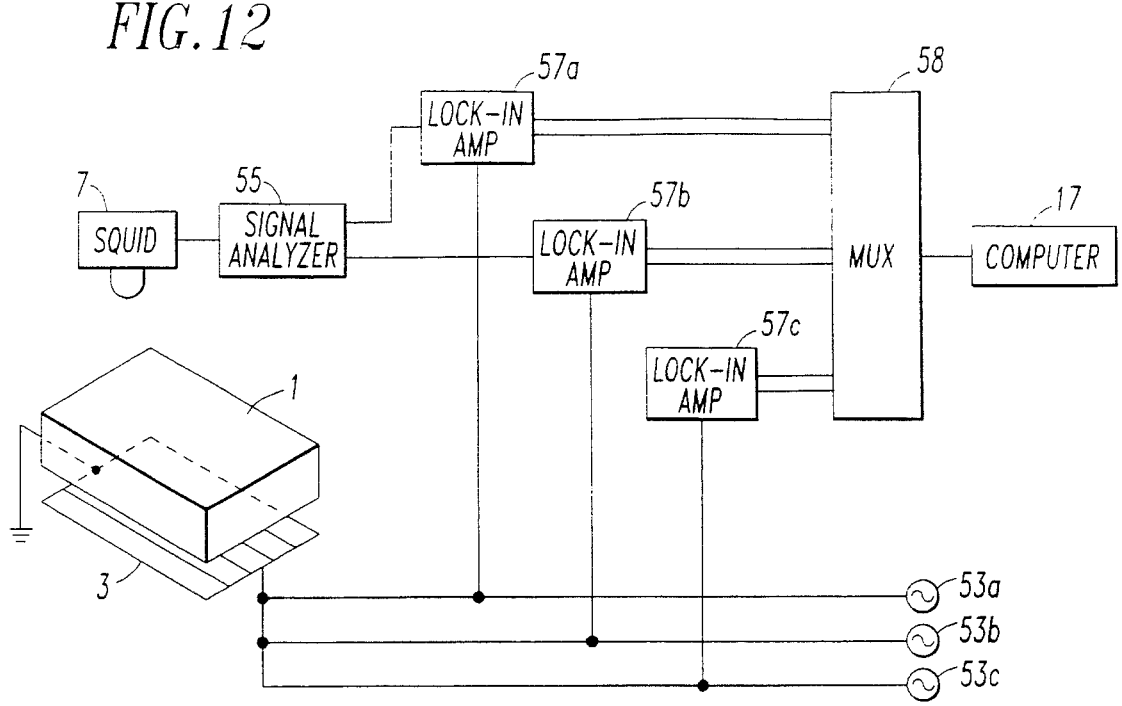
FIG. 12 is a schematic diagram of apparatus for application of the invention using three frequencies of induced eddy current.

FIG. 12 illustrates an arrangement for scanning the electrically conductive object 1 with sheet eddy currents at three different frequencies. The three frequencies generated by the frequency sources 53A–53C are applied to the induction member 3 to generate sheet eddy currents in the object 1 at the three different frequencies. The SQUID magnetometer 7 which scans the object, generates a single response signal containing contributions from the three frequencies in the z component of the magnetic field generated by the disturbed currents. The three frequency signals are extracted from the magnetometer signal by the signal analyzer 55 and each is applied to a two-phase lock-in amplifier 57A–57C. The signals from the respective sources 53A–53C are applied to the lock-in amplifiers 57A and 57C to produce in-phase and quadrature components of the respective detector signals which are utilized by the microcomputer 17 to generate output signals at the selected phase angles with respect to the respective sources.

Figure 13:
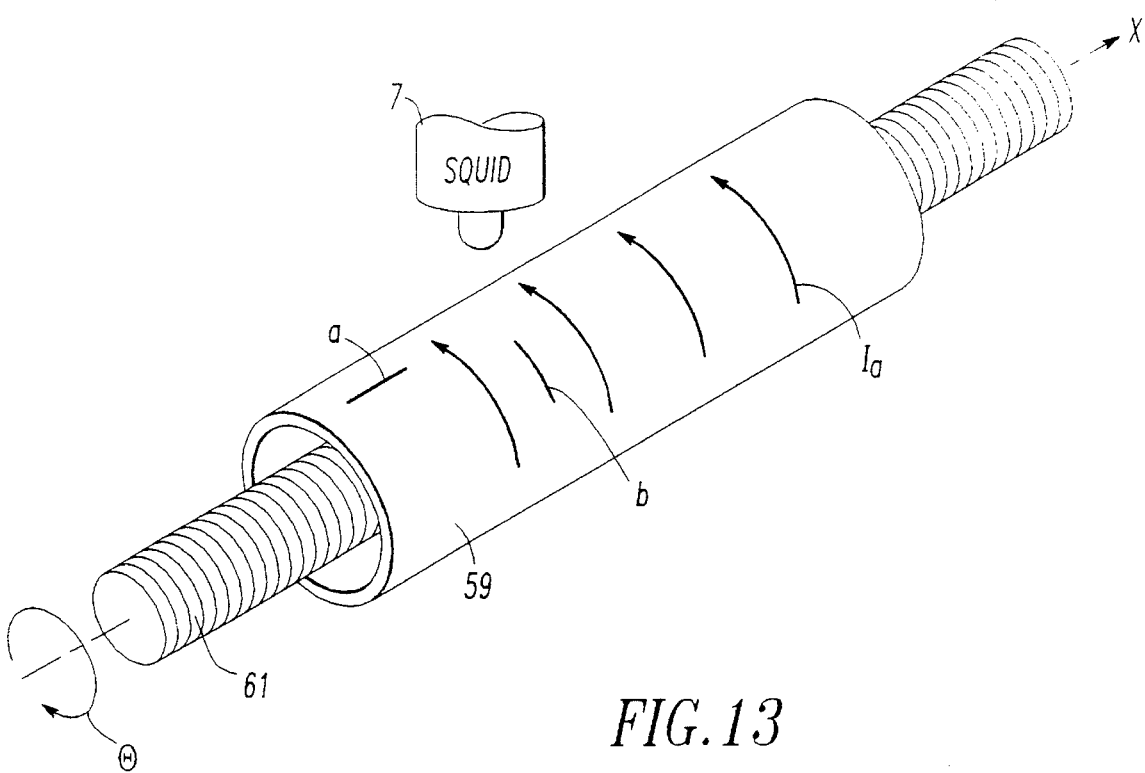
FIG. 13 is a schematic isometric view illustrating application of the invention to the detection of flaws in a tubular conducting member using an elongated solenoid as the induction member.

The invention can also be applied to testing an elongated object such as a cylindrical tube. As shown in FIG. 13, where the electrically conductive object is a long cylindrical tube 59, a solenoid 61 that is placed inside (or outside) the tube, induces an azimuthal eddy current $I_a$ inside the tube wall due to the change of magnetic flux through the tube. An infinitely long, homogeneously wound solenoid 61 that is concentric with the tube produces a uniform magnetic field along the tube axis near the surface of the tube. If the tube is also perfect and infinitely long, the induced eddy current is only a function of the radius. An ideal solenoid and a perfect tube do not produce any magnetic field in the radial direction. Thus the field detected by the SQUID magnetometer in the absence of a flaw should be zero when the axis of the pick-up coil is oriented radially with respect to the tube. For a tube containing flaws, the disturbed eddy current produces a magnetic signal in the radial direction, which can be detected by our SQUID magnetometer 7. Phase analysis, as described above, can be used to detect subsurface flaws, to reduce the background signal due to inperfect alignment between the solenoid 61 and the tube 59, and to reduce the effects of surface flaws to prevent masking of the subsurface flaws.

As the elongated solenoid 61 induces circumferential current $I_a$ in the tubular member 59, this arrangement is best for detecting flaws having a primarily longitudinal dimension such as the flaw a. Circumferential flaws such as b do not produce as large a signal with this arrangement since they are parallel to the current $I_a$ and therefore do not disturb the current as much.

Figure 14:
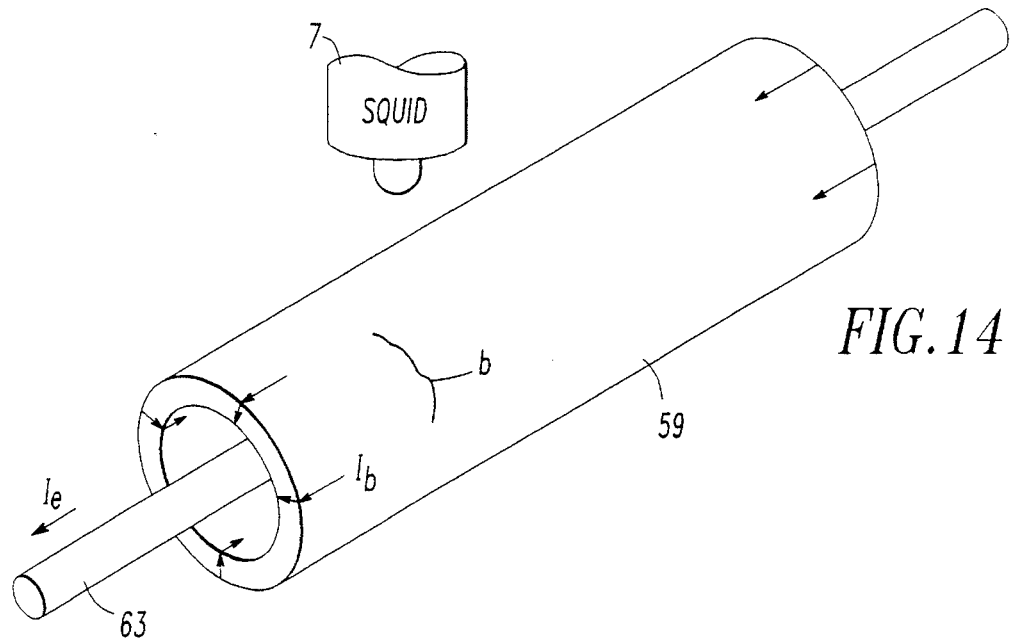
FIG. 14 is a schematic isometric view illustrating use of a rod inductor to detect circumferential flaws in the tubular member of FIG. 13.

For detecting flaws having a primarily circumferential dimension, the arrangement in FIG. 14 should be used. Here a conductive rod 63 is inserted concentrically within the tubular member 59. A current $I_c$ in the rod 63 induces a current $I_b$ in the tube which flows longitudinally in the direction opposite to the inducing current $I_c$ on the inner surface of the tubular member 59 and in the opposite longitudinal direction on the outer surface. This longitudinal eddy current $I_b$ generates a larger signal which can be detected by the SQUID 7 in response to flaws such as b having a primarily circumferential dimension. Again, phase analysis can be used to enhance sub-surface flaws. Both the solenoid inductor and the rod inductor should be used to assure the best opportunity for detection of flaws of unknown orientation.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. A method of detecting flaws below a generally smooth surface of an electrically conductive object, said method comprising the steps of:

generating a uniformly distributed ac current generally parallel to and extending over said generally smooth surface of said electrically conductive object to induce a sheet ac eddy current in said object generally parallel to said generally smooth surface;

generating a detection signal representative of a component of a magnetic field generated by said sheet eddy current in said electrically conductive object in the presence of a flaw which is substantially perpendicular to said generally smooth surface; and determining a magnitude of said detection signal at a phase angle with respect to said uniformly distributed ac current selected for detection of a flaw at a selected depth below said generally smooth surface.

2. The method of claim 1 wherein said step of determining the magnitude of said detection signal at a selected phase angle with respect to said uniformly distributed ac current comprises adjusting said phase angle over a range of phase angles selected to detect the flaws over a range of depths below said generally smooth surface.

3. The method of claim 2 comprising generating said detection signal over a selected portion of said generally smooth surface and determining the magnitude of said detection signal over said range of phase angles over said portion of said generally smooth surface.

4. The method of claim 1 wherein said step of determining the magnitude of said detection signal at a selected angle with respect to uniformly distributed ac current comprises determining an in-phase component and a quadrature component of said detection signal with respect to said uniformly distributed ac current, and determining said magnitude of said detection signal at said selected phase angle with respect to said uniformly distributed ac current from said in-phase and quadrature components.

5. The method of claim 4 comprising determining said magnitude of said detection signal for a range of selected phase angles with respect to said uniformly distributed ac current from said in-phase and quadrature components.

6. The method of claim 5 comprising determining said magnitude of said detection signal for a range of selected phase angles with respect to said uniformly distributed ac current from said in-phase and quadrature components over a selected portion of said generally smooth surface.

7. The method of claim 1 wherein said step of generating a detection signal comprises generating said detection signal over a selected portion of said generally smooth surface and wherein said determining a magnitude of said detection signal comprises determining the magnitude of said detection signal at the selected phase angle with respect to said uniformly distributed ac current over said selected portion of said generally smooth surface.

8. The method of claim 1 comprising generating a uniformly distributed ac current generally parallel to said generally smooth surface at a plurality of frequencies, generating detector signals representative of a component of a magnetic field substantially perpendicular to said generally smooth surface for each frequency, and determining the magnitude of said detector signal at selected phase angles with respect to the uniformly distributed ac currents for each frequency.

9. The method of claim 8 comprising generating said sheet eddy currents at said plurality of frequencies for a plurality of angular orientations about an axis substantially perpendicular to said generally smooth surface, generating said detection signals for each frequency for each angular orientation, and determining the magnitude of said detector signals at said selected phase angles for each frequency for each angular orientation.

10. The method of claim 1 wherein said step of generating said uniformly distributed ac current comprises generating a uniformly distributed ac current for plurality of angular orientations about an axis substantially perpendicular to said generally smooth surface, generating said detection signal for each angular orientation, and determining a magnitude of said detector signals for each of said angular orientations.

11. The method of claim 1 wherein said electrically conductive object is elongated and said step of generating a uniformly distributed current comprises an elongated solenoid concentric with said elongated member for inducing a circumferential sheet eddy current in said elongated member.

12. Apparatus for detecting flaws below a generally smooth surface of an electrically conductive object, comprising:
an induction member carrying a uniformly distributed ac current positioned adjacent said smooth surface of said electrically conductive object to induce a sheet eddy current in said electrically generally conductive object parallel to and extending over said generally smooth surface;
detector means generating a detector signal representative of a component substantially perpendicular to said generally smooth surface of a magnetic field generated by said sheet eddy current in said electrically conductive object in the presence of a flaw; and
phase sensitive means responsive to said ac current and said detection signal generating an output signal representative of a magnitude of said detection signal at a phase angle with respect to said ac current carried by said induction member selected for detection of a flaw at a selected depth below said generally smooth surface.

13. The apparatus of claim 12 wherein said phase sensitive means comprises means generating an in-phase and quadrature component of said detector signal, and output means generating output signals from said in-phase component and said quadrature component.

14. The apparatus of claim 13 wherein said output means comprises means generating an output signal for a range of selected phase angles with respect to said uniformly distributed ac current from said in-phase component and said quadrature component.

15. The apparatus of claim 14 wherein said detector means comprises a SQUID.

16. The apparatus of claim 12 wherein said induction member comprises a plurality of parallel conductive members and means connecting said parallel conductive members in series.

17. The apparatus of claim 12 wherein said detector means comprises means scanning relative to said electrically conductive object to generate said detector signal over at least a selected portion of said electrically conductive object, and wherein said phase sensitive means generates said output signal representative of the magnitude of said detector signal at said selected phase angle relative to said uniformly distributed ac current over said selected portion of said electrically conductive object.

18. The apparatus of claim 17 wherein said detector means comprises a SQUID.

19. The apparatus of claim 12 wherein said induction member comprises means rotatable about an axis generally perpendicular to said generally smooth surface of said electrically conductive object for generating said uniformly distributed ac current at a plurality of orientations, said detector means generates said detector signal for said plurality of orientations, and said phase sensitive means generates said output signal for said respective orientations.

20. The apparatus of claim 12 wherein said induction member carries a uniform ac current at a plurality of frequencies to induce a sheet eddy current at said plurality of said frequencies in said electrically conductive object, wherein said detector means comprises means generating a detector signal for each frequency; and wherein said phase sensitive means comprises means generating an output signal representative of a magnitude of said detection signals for selected phase angles with respect to the ac current for each frequency.

21. The apparatus of claim 12 wherein said electrically conductive object is elongated and said induction member is an elongated solenoid concentric with said elongated electrically conductive object.

22. The apparatus of claim 12 wherein said electrically conductive object is tubular and said induction member is a rod concentric with said tubular elongated electrically conductive object.

* * * * *

UNITED STATES PATENT AND TRADEMARK OFFICE
CERTIFICATE OF CORRECTION

PATENT NO. : 5,610,517

DATED : March 11, 1997

INVENTOR(S) : YU P. MA and JOHN P. WIKSWO, JR.

It is certified that error appears in the above-identified patent and that said Letters Patent is hereby corrected as shown below:

In column 4, line 61, "$I_e$" should be --$I_s$--.

In column 5, line 63, "8" should be --$\delta$--.

In column 5, line 65 and line 67, "$\gamma$" should be --$\delta$--.

In column 6, line 1 and line 8, "$\gamma$" should be --$\delta$--.

In column 6, line 12, "$I_c$" should be --$I_e$--.

In column 8, line 30, "$_{min}$" should be --$_{mm}$--.

In column 8, line 39, "$(S_{pp},$" should be --$(S_{pp})$--.

In column 9, on lines 14, 24 and 36, "$\gamma$" should be --$\delta$--.

In column 10, line 14, "$I_8$" should be --$I_s$--.

Signed and Sealed this

Ninth Day of December, 1997

Attest:

BRUCE LEHMAN

Attesting Officer

Commissioner of Patents and Trademarks